(12) United States Patent
Love et al.

(10) Patent No.: US 6,494,859 B2
(45) Date of Patent: *Dec. 17, 2002

(54) METHODS USING PRESSURE TO OBTAIN FLUIDS AND CELLULAR MATERIAL FROM BREAST DUCTS

(75) Inventors: Susan M. Love, Pacific Palisades, CA (US); David Hung, Belmont, CA (US); Xuanmin He, Palo Alto, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/301,058

(22) Filed: Apr. 28, 1999

(65) Prior Publication Data

US 2002/0019017 A1 Feb. 14, 2002

Related U.S. Application Data

(63) Continuation-in-part of application No. 09/067,661, filed on Apr. 28, 1998, now Pat. No. 6,221,622.

(51) Int. Cl.⁷ ................................................ A61M 1/00
(52) U.S. Cl. ........................ 604/28; 604/19; 604/27; 604/48; 604/73; 604/74; 604/75; 604/76
(58) Field of Search .......................... 424/277.1, 422; 435/7.1, 7.23; 119/14.19–14.25; 604/28, 30, 54, 73–76, 433, 19, 27, 48

(56) References Cited

U.S. PATENT DOCUMENTS 5,413,558 A   5/1995  Paradis .................... 604/101

FOREIGN PATENT DOCUMENTS

WO   WO97/05898   2/1997
WO   WO/99/13917  3/1999

OTHER PUBLICATIONS

Okazaki et al. Relationship between cytologic results and the extent of intraductal spread in nonpalpble breast cancers with nipple discharge. Tumor Research. vol. 31 (1996) pp. 89–97.*

Raul A. Leborgne, "The Breast in Roentgen Diagnosis", Impressora Uruguaya S.A.—Juncal [51], Montevideo (Uruguay), 1953.

Akira Okazaki, "Diagnosis of Nonpalpable Breast Cancer By Ductoscopy: Comparison of Imaging and Histological Findings", Nyugan no Rinsho (Clinical Breast Cancer) 4(4):587–594 (1989).

Claude Feige, "Dynamic Morpho–Cyto–Echography and the Echographic Galactoscopy Endo–Ductal Sample Intrinsic and Extrinsic Markers in the Detection of Breast Cancers", *Ultrasound in Med. & Biol.*, vol. 14, Sup. 1, pp. 97–108, 1982.

Jeffrey A. Fisher, "Our Medical Future: Breathroughs in Health and Longevity by the Year 2000 and Beyond", Copyright 1992, book published by Pocket Books, New York, NY, U.S.A., pp. 136–141.

S. H. Barsky et al., "Pathologic Analysis Of Breast Duct Endoscoped Mastectomies" Laboratory Investigation, Modern Pathology, Annual Meeting Abstracts (1996) p. 15A, Abstract No. 67.

C. Fabian et al., "Prevalence Of Abnormal Biomarkers In Fine Needle Breast Aspirates In A High Risk Population: Potential For Use In Risk Prediction" Proc. Ann. Meet. Am. Assoc. Cancer Res. (1993) 34:A1556.

Carol J. Fabian et al., "Biomarker and Cytologic Abnormalities In Women At High and Low Risk For Breast Cancer", Journal Of Cellular Biochemistry, 17G:153–160 (1993).

M. Falardeau et al., "Selective Galactophorectomy For Mono–Orificial Nipple Discharge Without Associated Mass: Technique and Results. Apropos Of Seventy-Three Cases", Database Medline 'Online', US National Library Of Medicine, Bethesda, Maryland, USA, (Abstract) and [Annales De Chirurgie, (1991) 45(9)796–801, Journal Code: 50E. ISSN: 0003–3944.].

C. Feige, "Dynamic Morpho–cyto–echography and the Echographic Galactoscopy Endo–ductal sample. Intrinsic and Extrinsic Markers in the Detection of Breast Cancers", Database Medline 'Online', US National Library of Medicine, Bethesda, Maryland, USA, (Abstract) AN=8904507 and ["Ultrasound in Medicine and Biology", (1998) 14 Suppl 1 97–108. Journal Code: WNE. ISSN: 0301–5629, United Kingdom].

(List continued on next page.)

*Primary Examiner*—James Housel
*Assistant Examiner*—Uleike Winkler
(74) *Attorney, Agent, or Firm*—Gates & Cooper LLP

(57) ABSTRACT

Methods, kits, and apparatus for obtaining cellular, chemical, and other materials from breast ducts are described. A single milk duct is accessed and washed with a washing fluid to obtain marker materials from the lining the duct. The washing fluid is then collected, and the marker materials in the washing fluid identified and analyzed. Usually, the washing fluid is introduced using a syringe through a lumen of a dual-lumen catheter. The ductal volume is filled with the washing fluid and excess fluid flows outwardly through a second lumen of the dual-lumen catheter, from which it is collected. Methods and kits provide for collection of fluid and cells by a lavage procedure that includes applying external pressure to the breast to improve the yield of fluid and cells from the breast duct.

15 Claims, 6 Drawing Sheets

OTHER PUBLICATIONS

M.F. Hou et al., "A Simple Method Of Duct Cannulation and Localization For Galactography Before Excision In Patients With Nipple Discharge", Radiology, (May 1995), 195(2) 568–9, Journal Code: OSH. ISSN: 0033–8419, XP002091599, United States.

Shuhei Imayama et al., "Presence Of Elevated Carcinoembryonic Antigen On Absorbent Disks Applied To Nipple Area Of Breast Carcinoma Patients" Cancer (1996)78(6):1229–1234.

Tomoaki Katamine et al., "Determination Of Cancer–Associated Antigens In Body Fluid Secreted From Nipple" Chemical Abstracts, vol. 114, No. 9, Mar. 4, 1991, 2pp, and [JP 02 280061 A, Mochida Pharmaceutical Co., Ltd., Japan].

Ricki Lewis, "Technique Probes Breast Ducts For Cancer Cells" Biophotonics International (May/Jun. 1997) pp. 27–28.

Susan M. Love, "Breast Duct Endoscopy: A Pilot Study Of A Potential Technique For Evaluating Intraductal Disease" 15th Annual San Antonio Breast Cancer Symposium, San Antonio, TX (1996) pp. 180, Abstract No. 197.

Susan M. Love et al., "Breast–Duct Endoscopy To Study Stages Of Cancerous Breast Disease" The Lancet (1996) 348:997–999.

Masujiro Makita et al., "Duct Endioscopy and Endoscopic Biopsy In The Evaluation Of Nipple Discharge" Breast Cancer Research and Treatment (1991) 18:179–187.

S. Naran et al., "Cytologic Diagnosis Of Papillary Carcinoma Of The breast In Needle Aspirates", Database Medline Online, US National Library Of Medicine, Bethesda, Maryland, U.S.A., An=88242405, Database Accession No. 88242405 XP002114398 (Abstract) and [Diagnostic Cytopathology, (Mar. 1988) 4(1) 33–7].

Akira Okazaki et al., "Fiberoptic Ductoscopy Of The Breast: A New Diagnostic Procedure For Nipple Discharge" Jpn. J. Clin. Oncol. (1991) 21(3):188–193.

Nicholas L. Petrakis, "Physiologic, Biochemical and Cytologic Aspects Of Nipple Aspirate Fluid" Breast Cancer Research and Treatment (1986) 8:7–19.

Nicholas L. Petrakis et al., "Letters To The Editor: Prognostic Significance Of Atypical Epithelial Hyperplasia In Nipple Aspirates Of Breast Fluid", The Lancet, August 29, 1987, pp. 505.

Nicholas L. Petrakis, "Studies On The Epidemiology and Natural History Of Benign Breast Disease and Breast Cancer Using Nipple Aspirate Fluid" Cancer Epidemiology, Biomarkers & Prevention (Jan./Feb. 1993) 2:3–10.

Nicholas L. Petrakis "Nipple Aspirate Fluid In Epidemiologic Studies Of Breast Disease" Epidemiologic Reviews (1993) 15:188–195.

Otto W. Sartorius, "Fluid Cytology and Contrast Ductography", pp. 79–89.

Otto W. Sartorius et al., "Contrast Ductography For Recognition and Localization Of Benign and Malignant Breast Lesions: An Improved Technique" Logan, W., Ed., Breast Carcinoma, New York, Wiley, (1977) pp. 281–300.

Otto W. Sartorius, "The Biochemistry of Breast Cyst Fluids and Duct Secretions" Breast Cancer Research and Treatment (1995) 35:255–266.

F. A. Weaver et al., "Management Of Postoperative Lymphatic Leaks By Use Of Isosulphan Blue [3]", Database EMBASE 'Online', Elsevier Science Publishers, Amsterdam, Netherlands, Databse Accession No. 91353868, XP002114397 (Abstract) and [Journal Of Vascular Surgery, (1991) 14/4 (566–567)].

Margaret R. Wrensch et al., "Breast Fluid Cholesterol and Cholesterol β–Epoxide Concentrations In Women With Benign Breast Disease" Cancer Res. (1989) 49:21682174.

Margaret R. Wrensch et al., "Factors Associated With Obtaining Nipple Aspirate Fluid: Analysis Of 1428 Women and Literature Review" Breast Cancer Research and Treatment (1990) 15:39–51.

Margaret R. Wrensch et al., "Breast Cancer Incidence In Women With Abnormal Cytology In Nipple Aspirates Of Breast Fluid" Am. J. Epidemiol. (1992) 135(2):130–141.

Margaret R. Wrensch, et al., "Breast Cancer Risk Associated With Abnormal Cytology In Nipple Aspirates Of Breast Fluid and Prior History Of Breast Biopsy", American Journal Of Epidemiology, vol. 137, No. 8, 1993, pp. 829–833.

M. Cukierfajn et al., "Intragalactophoric Aspiration: Description of a Cytologic Examination Complementary to Galactography and First Results Obtained", J. belge Radiol.—Belgish Tijdschr. Radiol., 66:101–106, (1983).

* cited by examiner

METHODS USING PRESSURE TO OBTAIN FLUIDS AND CELLULAR MATERIAL FROM BREAST DUCTS

This application is a continuation-in-part of application Ser. No. 09/067,661, filed on Apr. 28, 1998, now U.S. Pat. No. 6,221,622, the contents of which are incorporated herein by reference.

This invention was made with Government support under contract DAMD 17-96-C-6117. The government has certain rights in this invention.

BACKGROUND OF THE INVENTION

1. Field of the Invention

The present invention relates generally to medical methods and apparatus for obtaining fluids and cellular materials from a patient. More particularly, the present invention relates to methods and apparatus for obtaining epithelial cells from the lining of a breast milk duct.

Breast cancer is the most common cancer in women, with well over 100,000 new cases being diagnosed each year (see e.g. Goodson W H & King E B, *Chapter* 4: *Discharges and Secretions of the Nipple*, The Breast: Comprehensive Management of Benign and Malignant Diseases 2nd Ed. vol 2, Bland & Kirby eds. W. B. Saunders Co, Philadelphia, Pa. pp. 51–74, (1998)). Even greater numbers of women, however, have symptoms associated with breast diseases, both benign and malignant, and must undergo further diagnosis and evaluation in order to determine whether breast cancer exists. To that end, a variety of diagnostic techniques have been developed, the most common of which are surgical techniques including core biopsy and excisional biopsy. Recently, fine needle aspiration (FNA) cytology has been developed which is less invasive than the surgical techniques, but which is not always a substitute for surgical biopsy.

A variety of other diagnostic techniques have been proposed for research purposes (see e.g. Sukumar et al., Molecular Medicine Today. 2(11):453–9, (1996); Sukumar et al., Mutation Research. 333(1–2):37–44, (1995)). Of particular interest to the present invention, fluids from the breast ducts have been externally collected, analyzed, and correlated to some extent with the risk of breast cancer. Such fluid collection, however, is generally taken from the surface of the nipple and includes material from all of the ductal structures. Information on the condition of an individual duct is generally not provided. Information on individual ducts can be obtained through cannulation and endoscopic or fluoroscopic examination, but such examinations have been primarily in women with nipple discharge or for research purposes and have generally not examined each individual duct in the breast.

Since breast cancer usually arises from a single ductal system and exists in a precancerous state for a number of years, endoscopy in and fluid collection from individual breast ducts holds great diagnostic promise for the identification of intermediate markers. Of particular interest to the present invention, it would be of great value to be able to reliably collect ductal fluids and cellular and non-cellular marker materials (e.g. epithelial and other cells as well as proteins, carbohydrates, and other non-cellular marker materials) from the individual breast ducts on a duct-by-duct basis. By examining the collected marker materials, cancerous and pre-cancerous conditions within each duct could be identified at a very early stage. Moreover, by associating the condition with a specific duct, treatment could be directed specifically at that duct in an attempt to enhance the effectiveness of the treatment and minimize trauma to the patient.

The ability to perform such diagnostic techniques, however, has been limited. Heretofore, it has been very difficult to identify ductal orifices in a reliable and consistent manner. That problem, however, has been addressed by the invention reported in co-pending, commonly assigned application Ser. No. 08/931,786, filed on Sep. 16, 1997, the full disclosure of which is incorporated herein by reference. By labeling the ductal orifices, the location of the entry orifice for each duct can be established.

Even though access to all of the ducts in a breast can now be achieved, successful diagnostic methods will depend on the ability to collect cellular and non-cellular materials from at least, most, and preferably all, regions of each ductal network. Breast ducts have highly complex and convoluted three-dimensional geometries, with more remote portions of the network having increasingly smaller diameters. Thus, obtaining representative material samples from throughout a ductal network represents a significant challenge.

Prior attempts to obtain cellular material from individual breast ducts have been only partly successful. As reported by the inventor herein, in Love and Barsky (1996) *The Lancet* 348:997–999 (1996), breast ducts have been cannulated with a rigid cannula and instilled with very small volumes (0.2 ml to 0.5 ml) of saline. Saline was recovered separately through a capillary tube, and cellular material recovered from the saline. It was not clear, however, if cellular material was recovered from most or all portions of the ductal network. Unless such representative samples can be obtained, reliable diagnostics cannot be performed. While the paper proposes development of a two-lumen catheter, no such catheter or its use is described in the publication.

For these reasons, to enable the performance of ductal diagnostic techniques, it will be useful to provide methods and apparatus which permit the collection of fluids and marker materials from individual ductal networks in a reliable and consistent fashion. Such methods should be minimally traumatic to the patient, should be useful for routine screening in at least high-risk patients, and should provide cellular and non-cellular materials suitable for reliable detection of cancerous and pre-cancerous conditions. At least some of these objectives will be met by the invention described hereinafter.

2. Description of the Background Art

Publications by the inventor herein relating to breast duct access include Love and Barsky (1996) Lancet 348: 997–999; Love (1992) "Breast duct endoscopy: a pilot study of a potential technique for evaluating intraductal disease," presented at 15th Annual San Antonio Breast Cancer Symposium, San Antonio, Tex., Abstract 197; Barsky and Love (1996) "Pathological analysis of breast duct endoscoped mastectomies," Laboratory Investigation, Modern Pathology, Abstract 67. A description of the inventor's earlier breast duct access work was presented in Lewis (1997) Biophotonics International, pages 27–28, May/June 1997.

Nipple aspiration and/or the introduction of contrast medium into breast ducts prior to imaging are described in Sartorius (1995) Breast Cancer Res. Treat. 35: 255–266; Sartorius et al. (1977) "Contrast ductography for the recognition and localization of benign and malignant breast lesions: An improved technique," in: Logan (ed.), Breast Carcinoma, New York, Wiley, pp. 281–300; Petrakis (1993) Cancer Epidem. Biomarker Prev. 2(1): 3–10; Petrakis (1993) Epidem. Rev. 15: 188–195; Petrakis (1986) Breast Cancer Res. Treat. 8: 7–19; Wrensch et al. (1992) Am. J. Epidem. 135(2): 130–141; Wrensch et al. (1990) Breast Cancer Res. Treat. 15: 39–51; and Wrensch et al. (1989) Cancer Res. 49: 2168–2174. The presence of abnormal biomarkers in breast aspirates is described in Fabian et al. (1993) Proc. Ann. Meet. Am. Assoc. Cancer Res. 34: A1556; Wrensch et al., American Journal of Epidemiology. 137(8):829–33, (1993) and Petrakis et al., Lancet. 2(8557):505, (1987). The use of a rigid 1.2 mm ductoscope to identify intraductal papillomas in women with nipple discharge is described in Makita et al. (1991) Breast Cancer Res. Treat. 18: 179–188. The use of a 0.4 mm flexible scope to investigate nipple discharge is described in Okazaki et al. (1991) Jpn. J. Clin. Oncol. 21: 188–193. The detection of CEA in fluids obtained by a nipple blot is described in Imayama et al. (1996) Cancer 78: 1229–1234. Delivery of epithelium-destroying agents to breasts by ductal cannulation is described in WO 97/05898.

A company called Diagnostics, Inc. formed in 1968, produced devices to obtain breast ductal fluid for cytological evaluation. The devices included a breast duct catheter to infuse fluid into and collect fluid from individual ductal orifices. The devices were sold prior to May 28, 1976, for the purpose of collecting breast ductal fluid for cytological evaluation.

SUMMARY OF THE INVENTION

The present invention provides improved methods, kits, and other apparatus for obtaining fluids, marker substances, cellular material, and the like (referred to hereinafter as "marker materials") from single milk ducts in the breasts of human female patients. In particular, the methods of the present invention permit reliable washing and retrieval of marker materials from an entire network of a single milk duct to enable screening, diagnosis, and monitoring of diseases associated with the lining of the milk duct, particularly for identifying cancer and pre-cancerous conditions. As the marker materials are obtained entirely from a single ductal network, diagnosis can be made on a duct-by-duct basis. By obtaining specimens from each one of the multiple ductal networks in a breast, however, the presence of disease or increased likelihood of disease in the entire breast can also be determined.

In a first aspect of the present invention, a method for obtaining marker materials from a milk duct of a breast comprises locating a single milk duct, typically by labeling a ductal orifice present in the nipple of the breast. A washing fluid, typically saline, is introduced into the duct so that it passes substantially throughout the entirely ductal network, preferably without rupturing the duct. At least a portion of the washing fluid is then collected from the duct, and marker materials which may be present in the collected fluid (including fluids which might otherwise be secreted) are identified. While in some cases it may be desirable to collect specimens from only a single ductal network, it will usually be preferred to repeat the steps in order to identify the presence of marker materials in each of the ductal networks present in the breast. Cellular marker materials may comprise epithelial cells from the lining of the duct while the fluids will comprise normally secreted and non-secreted fluids present in the ducts. The epithelial and other cells obtained by the method will usually be morphologically histochemically, and/or immunohistochemically examined to determine if they are abnormal and to assess the likelihood of a cancer or pre-cancerous condition present in the cellular lining of the duct. Non-cellular marker materials include proteins, peptides, and other chemical species which may be secreted or otherwise released into a duct in response to a disease or other condition to be identified.

In a further aspect of the present invention, a preferred method for obtaining marker materials from a milk duct of a breast comprises locating at least one of the ductal orifices on the breast nipple. A dual-lumen catheter is then introduced through the orifice and into the ductal passage, usually over a guidewire. A washing fluid is then introduced through one of the lumens into the duct. Sufficient fluid is introduced so that the fluid will substantially fill the ductal volume and will then pass outwardly through the other of the catheter lumens so that it may be collected externally to the breast. Marker materials, such as epithelial and other cells, present in the collected washing fluid may then be isolated, detected and/or examined, as generally described above. Additionally, the ductal fluids present in the ducts prior to introduction of the washing fluid will be diluted and collected and may be examined for the presence of both small molecules and macromolecules, including proteins, carbohydrates, and other potential disease markers.

The volume of washing fluid introduced into the ductal network will usually be at least 5 ml, preferably being from 5 ml to 25 ml, usually being about 10 ml. The washing fluid will typically be introduced through the catheter lumen using a syringe at a generally low pressure which will not result in rupture of the ductal network. The washing fluid will be introduced over a relatively short time period, typically from 1 minute to 5 minutes, and will continue to be introduced even after the initial portions of the fluid begin to emerge from the second catheter lumen. As before, the method will usually be repeated for each of the ductal networks present in the breast.

The invention further provides an improved method for obtaining fluid and cellular material from distal areas of the ductal architecture of a breast milk duct. The method comprises introducing a washing fluid into a milk duct, applying external pressure to the breast, collecting at least a portion of the washing fluid from the duct, wherein the portion of the washing fluid collected comprises fluid and cells from the duct. The application of external pressure can be manual or mechanical. The external pressure can effectively mix fluid, cells and other ductal contents together in a duct. The external pressure can be applied beginning at the base of the breast and working up to the areola and nipple regions of the breast. Introducing a washing fluid can comprise continuous, or intermittent infusion of washing fluid over a period of time. The external pressure may be applied to the breast periodically, continuously, or cyclically during infusion of the wash fluid. Introducing and collecting can comprise access of a breast duct by an access tool having at least one lumen. Collecting can comprise applying suction to an outflow lumen of a dual lumen catheter to draw fluid out from the duct. The washing fluid can comprise a mixture of a gas (such as air or nitrogen) and fluid.

The invention provides a method for obtaining fluid and cellular material including fluid and cellular material from distal areas of the ductal architecture of a breast milk duct comprising introducing a washing fluid into a milk duct, and providing continuous or intermittent infusion of the wash fluid for a period of time; applying external pressure to the breast and repeating application of external pressure periodically, continuously, or cyclically during infusion of the wash fluid; collecting the washing fluid from the duct during the infusion and application of external pressures, wherein the washing fluid collected comprises fluid and cells originating from the duct. Introducing and collecting can comprise access of a breast duct by an access tool having at least one lumen. Collecting can comprise applying suction to an outflow lumen of a dual lumen catheter to draw fluid out from the duct. The washing fluid can comprise a mixture of air and fluid.

The invention also provides a method of obtaining material from a milk duct in a breast of a patient comprising locating at least one ductal orifice on a nipple of the breast; introducing an access tool having at least one lumen through one of the ductal orifices and into the ductal passage; introducing a washing fluid through a lumen into the ductal passage; applying external pressure to the breast; collecting the washing fluid from the ductal passage through a lumen of the access tool during or after fluid introduction and applying external pressure; and identifying materials present in the collected washing fluid. The washing fluid can comprise a mixture of air and fluid.

According to yet a further aspect of the present invention, a kit for obtaining marker materials from a breast duct comprises a dual-lumen catheter together with instructions setting forth a method for use as described above. The kit will usually further comprise a package, such as a pouch, tray, tube, box, or the like. The instructions for use may be printed on a separate piece of paper, or optionally may be printed in whole or in part on a portion of the packaging. Usually, the dual-lumen catheter will be sterilized and maintained in a sterile condition within the packaging. Optionally, other system components, such as guidewires, saline or other washing fluid(s), cell growth and maintenance media, cell fixation media, cell collection trays, or the like, could be provided as part of the kit.

The invention provides a kit for obtaining material from a milk duct of a breast, comprising an access tool having at least one lumen, and instructions setting forth a method for use of the access tool according to any of above described methods that comprise application of external pressure, and a container for the kit contents. The kit can also comprise reagents for washing, collection, preservation or analysis of ductal fluid.

DESCRIPTION OF THE SPECIFIC EMBODIMENTS

Figure 1:
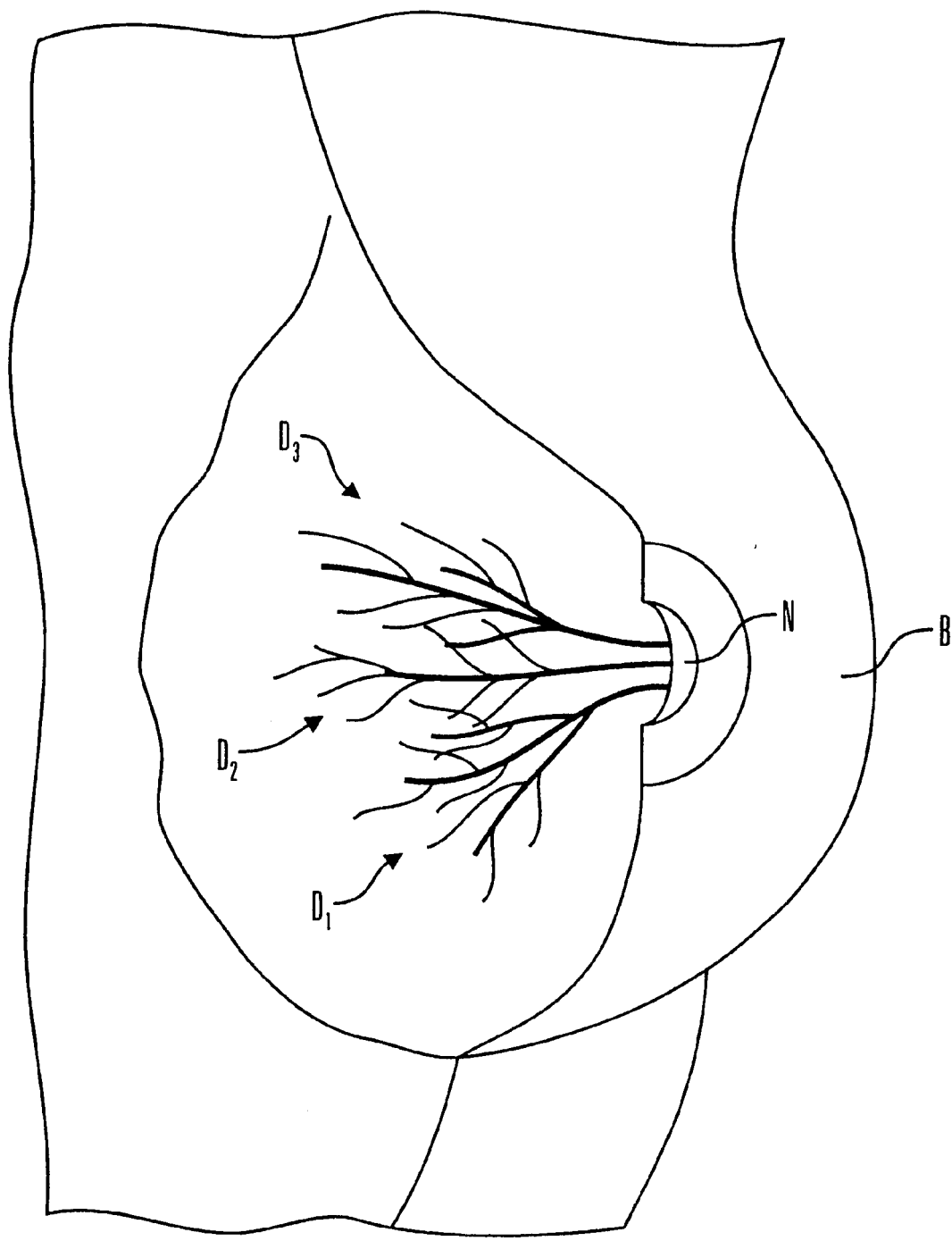
FIG. 1 is an anterior view of a human female breast, shown in section, and illustrating three of the six to nine ductal networks extending inwardly from the nipple.
Figure 2:
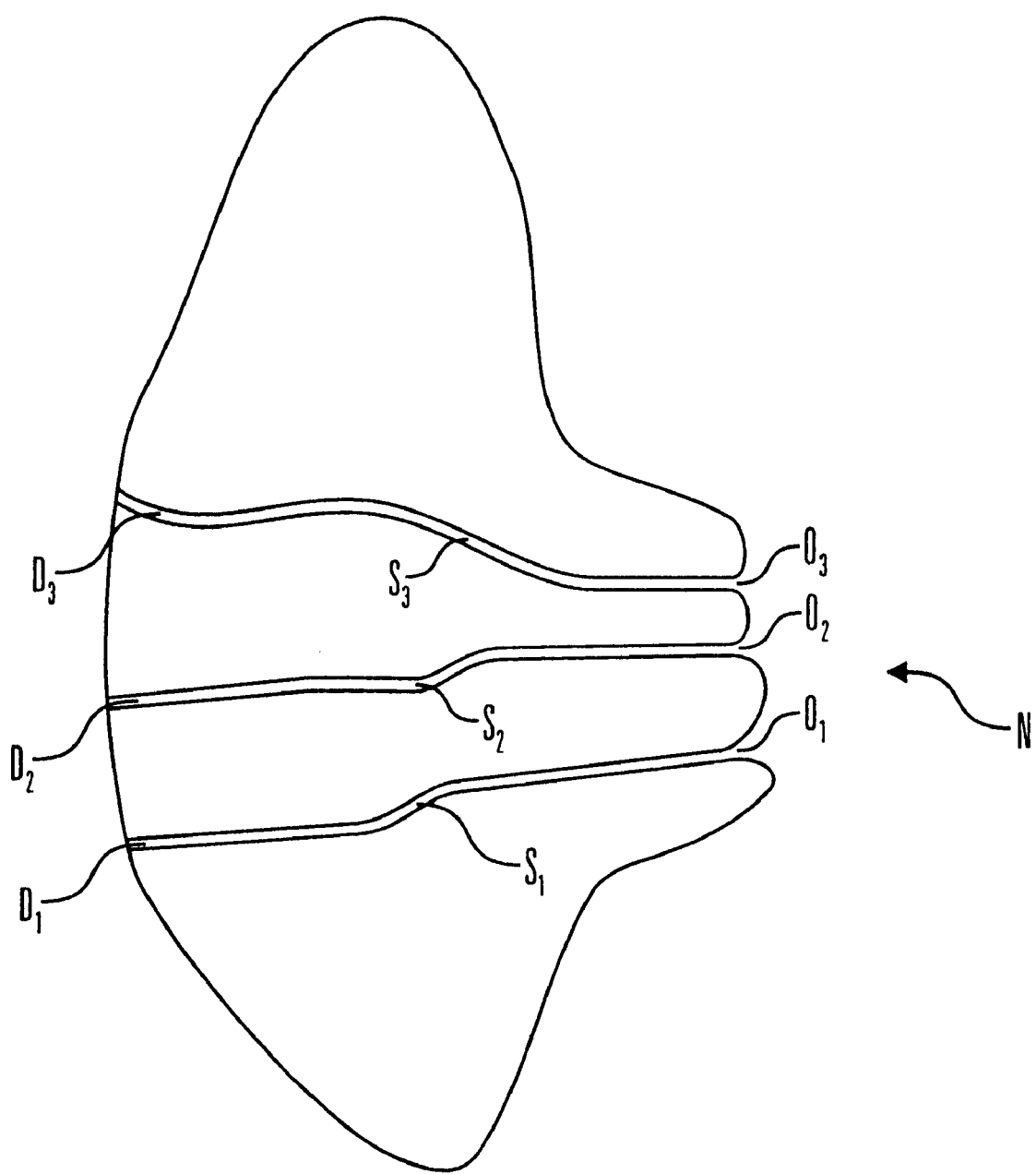
FIG. 2 is an enlarged view of the nipple of FIG. 1 illustrating the orifices leading to each of the three ductal networks.

The present invention comprises methods and kits for obtaining marker materials from one or more ductal networks in a human female breast. A typical breast B, as illustrated in FIG. 1, includes a nipple N and from six to nine ducts D. Three ductal networks D1–3 extending inwardly from the nipple N into the breast tissue are illustrated. As best seen in FIG. 2, each ductal network $D_{1-3}$ begins with an orifice $O_{1-3}$ which lies at the surface of the nipple N and extends inwardly through a ductal sinus $S_{1-3}$ and then into a branching network. Each network D comprises a series of successively smaller lumens which are arranged in complex, three-dimensional patterns. The networks of each duct will overlap within the breast tissue but will not be interconnected. The total volume of each network is usually in the range from 0.1 ml to 0.5 ml, but the walls are somewhat compliant so the internal volume may increase as fluid is introduced. The present invention relies on accessing the ductal network(s) through the orifice O of the duct D within the nipple N. Usually, there will be from six to nine orifices which open into a like number of ductal networks. Confirmation of the number and location of the ductal orifices can be made by labeling the nipple as described below.

The present invention relies on collecting endogenous ductal fluids and cellular and non-cellular marker materials from the individual ductal networks on a duct-by-duct basis. That is, fluids and marker materials are obtained from a single duct without obtaining material from any other ducts. This is in contrast to prior techniques which, in some instances, are able to obtain cellular and other materials from all milk ducts at once by applying a mild vacuum to the nipple. It should be noted, however, that in some instances such screening of all ducts in a single step may be appropriate in order to identify patients showing abnormalities for whom further, duct-specific testing according to the present invention is appropriate.

As a first step of the method herein, a location of at least one duct will be determined, typically by labeling all ductal orifices as described in co-pending application Ser. No. 08/931,786, the full disclosure of which has previously been incorporated herein by reference. Briefly, a portion of the epithelial lining present exposed at the ductal orifice may be labeled with a visible marker which allows the treating professional to identify the entry orifice for each of the ductal networks in the breast. Following identification of the ductal orifice, a washing fluid will be introduced into the duct in order to loosen and mobilize cellular material from the ductal lining, primarily epithelial cells from the lining. The washing fluid is introduced in an amount and a manner such that substantially the entire volume of the duct will be washed with the fluid in order to obtain a sample which is representative of the entire ductal network. Cellular components from the sample will usually be of the most interest, but ductal fluids and secreted molecular species (both small molecules and more usually biological macromolecules such as proteins and carbohydrates) may also be analyzed. The washing fluid carrying the cells and other materials is then collected, and the materials morphologically, histologically, immunohistologically, chemically, immunologically, enzymatically, or otherwise examined in order to determine any abnormal or disease conditions within the ductal network, particularly cancer or a pre-cancerous condition.

In the preferred embodiment, the washing fluid is introduced using a dual-lumen catheter which permits simultaneous introduction of the washing fluid and collection of excess washing fluid as it flushes back outwardly from the ductal network. The fluid being collected is usually not aspirated (since aspiration could collapse the duct), and instead the pressure of the introduced fluid is relied on to both flush the entire ductal network and expel the excess fluid through the other lumen of the cannula. Optionally, external pressure may be applied to the breast to enhance or expedite fluid collection. Typically, the fluid is introduced using a syringe, with the fluid being introduced at a relatively low rate, typically in the range from 0.1 ml/sec to 5 ml/sec, preferably from 0.5 ml/sec to 1 ml/sec. The total introduced volume of the washing fluid is typically at least 5 ml, typically being in the range from 5 ml to 25 ml, usually being about 10 ml, and optionally being greater. A preferred washing fluid is physiologic saline but contrast media and other physiologically acceptable, sterile fluids may also be used.

Figure 3:
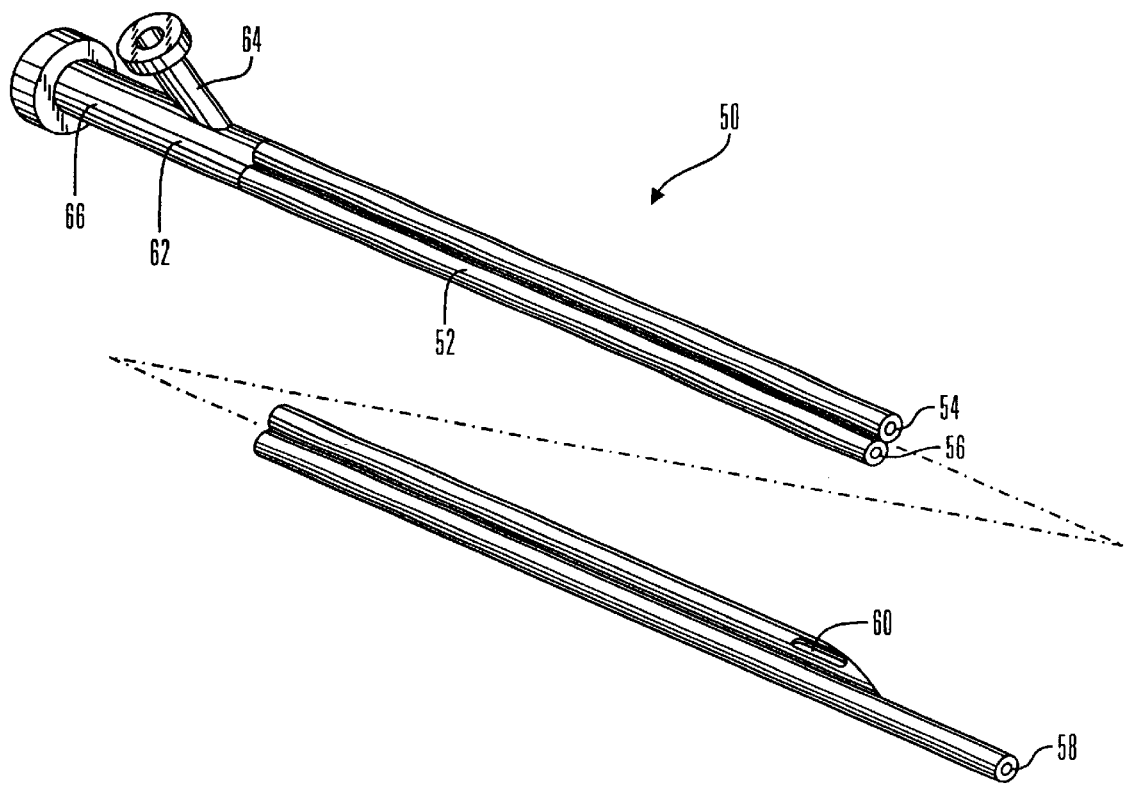
FIG. 3 is a perspective view of a dual-lumen catheter which is useful in performing the methods of the present invention.
Figure 4:
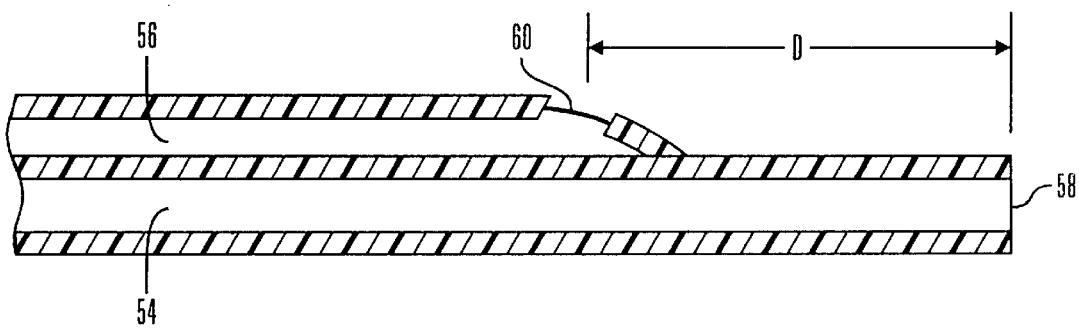
FIG. 4 is a detailed view of the distal end of the catheter of FIG. 3, shown in section.

An exemplary catheter 50 useful for performing the methods of the present invention is illustrated in FIGS. 3 and 4. The catheter comprises a catheter body 52, typically having a length in the range from 3 cm to 50 cm usually from 10 cm to 25 cm. The catheter body 52 includes at least a first lumen 54 and a second lumen 56. The first lumen 54 terminates in a distal port 58, as best seen in FIG. 4, while the second lumen terminates in a proximally located port 60, typically being located by a distance d which is approximately 0.1 cm to 1 cm, usually from 0.1 cm to 0.25 cm, proximal of the distal port 58. Catheter body 52 will have a relatively narrow diameter, typically having a maximum diameter in the dual-lumen region in the range from 0.8 mm to 2.5 mm, preferably being in the range from 0.8 mm to 1.2 mm. The diameter of the distal, single-lumen region may be less, as in the range from 0.5 mm to 1.5 mm, preferably from 0.6 mm to 1 mm. Proximal hub 62 includes a port 64 which is fluidly coupled to the second lumen 56 for delivering the washing fluid into the ductal network. Second port 66 is provided both for introducing the catheter over a guidewire and for collecting the washing fluid from the ductal network via port 58.

Figure 5:
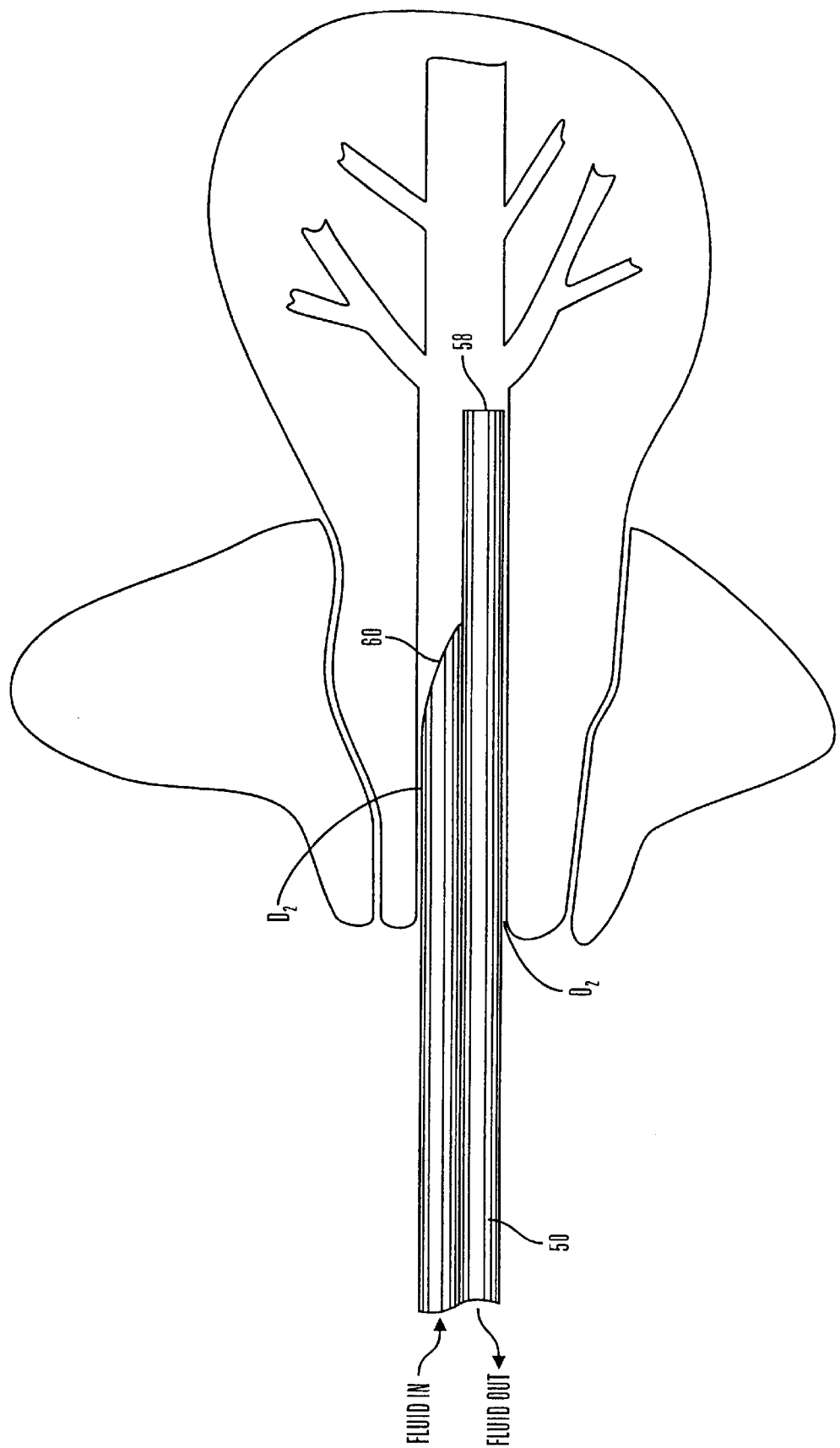
FIG. 5 illustrates use of the catheter of FIG. 3 in performing the method of the present invention in a single ductal network.
Figure 6:
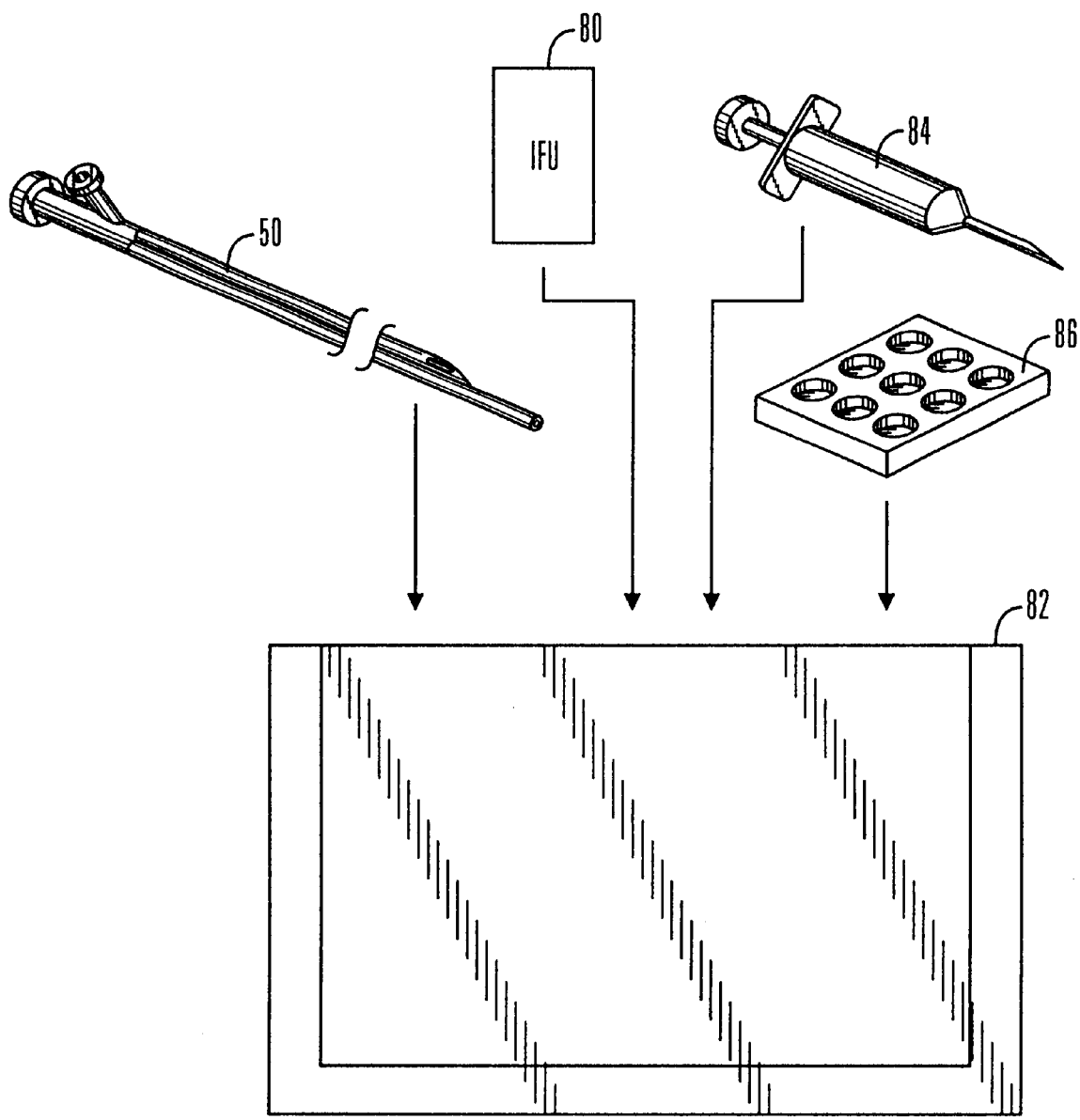
FIG. 6 illustrates a kit comprising a dual-lumen catheter and other system components, including instructions for use.

Referring to FIG. 5, use of the catheter 50 for collecting marker materials from a ductal network $D_2$ will be described. Usually, the ductal network $D_2$ will first be accessed with a guidewire, such as a conventional 0.014 inch guidewire (not shown). After the guidewire is introduced, typically by a distance in the range from 0.25 cm to 2.5 cm past the orifice $O_2$, the catheter 50 will be introduced over the guidewire by passing distal port 58 of the first lumen 54 over the external end of the guidewire. The distal port 58 is introduced into the ductal network $D_2$ typically to a depth of about 0.25 cm to 2.5 cm, usually about 0.75 cm to 1.5 cm. As discussed above, the second port 60 will be located proximally from the first port by a distance in the range from 0.1 cm to 1 cm, and will thus be closer to the orifice $O_2$. After the catheter 50 is in place, the guidewire will typically be withdrawn and the washing fluid introduced through the second lumen 56 via port 64 and opening 60. The washing fluid will flow into the ductal network and will generally reach most of the ductal volume, typically reaching at least 75% of the ductal volume, preferably at least 85%, and sometimes as much as 95%.

Alternatively, the guidewire and catheter 50 may be introduced simultaneously, typically with the distal tip of the guidewire extending a short distance ahead of the distal end of the catheter, usually about 0.1 cm to 1 cm. The guidewire is used to steer and the catheter 50 follows to the desired target location in the duct.

The volume of fluid introduced into the ductal network $D_2$ will be sufficiently large so that substantially the entire volume of the ductal network may be filled with the washing fluid and excess fluid will flow from the network as it is displaced by additional fluid input. Usually, only a small portion in the amount of washing fluid being introduced will be necessary to fill the ductal network, usually less than 1 ml, often less than 0.5 ml. The remaining fluid will continue to be introduced and will thus flush the cellular and other marker materials from the ductal network into the opening 58 in the first lumen 54. Thus, that fluid will pass outwardly through the catheter and may be collected from port 66 in the catheter. Preferably, no vacuum or other aspiration pressure will be applied to the catheter. Instead, the fluid will flow outwardly in response to the positive pressure created by the inflow of washing fluid, optionally with external pressure applied to the breast.

The invention further comprises a method for obtaining fluid and cellular material from breast milk ducts including obtaining fluid and cellular material from distal areas of the ductal architecture of a breast milk duct. The method comprises introducing a lavage or washing fluid into the duct. Optimally, the duct is substantially filled with a sufficient amount of washing fluid so that the duct is substantially filled washing fluid. The washing or lavage fluid can be e.g. saline, e.g. phosphate buffered saline (PBS) or normal saline. Once the duct has been filled with fluid (as can be determined e.g. when the inflow lumen meets resistance to infusion of more fluid) the practitioner can apply external pressure to the breast, and proceed with collecting the washing fluid or a portion of the washing fluid from the duct as a result of the external pressure. The application of external pressure can be manual or mechanical pressure applied to the breast. The mechanical pressure applied to the breast can be from a device designed to manipulate and squeeze the breast, e.g. a device having rollers, inflatable bladders, or other effective mechanism for applying external pressure to the breast. The manual pressure applied to the breast can comprise massaging the breast or squeezing the breast or a combination of both. The manual pressure can be applied as massaging and/or squeezing either in the same action (i.e. massaging and squeezing in a single action) or in alternating actions (i.e. first massaging for a period of time then squeezing for a period of time). The massaging action can comprise manual massaging, e.g. comprising gentle pressure to the breast in a kneading action in order to effectively mix fluid, cells and other ductal contents together in the ducts. The squeezing action can comprise manual squeezing to encourage the contents of the milk ducts to travel to the ductal orifices from distal regions of the ductal architecture. The massaging and/or squeezing can be accomplished by means other than manual pressure, e.g. automated or machine driven application of external pressure to the breast.

The application of external pressure to the breast comprising massaging and/or squeezing can comprise massaging first, then squeezing, followed by repeated cycles of massaging and then squeezing. Alternatively, the external pressure may be applied in an action that combines massaging with squeezing, perhaps applied periodically as the breast is infused with lavage fluid and emptied. Alternatively, the external pressure may be applied by application of massaging during fluid infusion, followed by squeezing once a breast duct is full. The massaging and squeezing may also be applied continuously or nearly continuously during infusion and collection of the lavage fluid from the breast ducts. Massaging and squeezing actions applied to the breast are designed to mix the fluid and ductal contents together in the duct (by massaging) and to coax the fluid and other ductal contents to the ductal orifice (by squeezing). Optimally, the fluid and ductal contents are retrieved and retrievable by this method from all areas of the breast milk ducts, including from the distal regions of the ductal architecture. Manual massaging and squeezing provide substantial control of pressure and positioning during the process of applying external pressure. Massaging action is designed to mix the ductal contents including the fluids and cells in the ducts. Squeezing can begin at the base of the breast and work upwards towards the areola and nipple. Techniques for massaging and squeezing (especially manual massaging and squeezing) can be modified for breast size and patient sensitivity as needed during the process.

The washing fluid to be collected can be directed from the duct to an outflow lumen (e.g. when a dual lumen catheter is used) or can be collected in any other suitable manner including a tube at an outflow lumen or a tube or other collection device at the ductal orifice. At least a portion of the washing or lavage fluid is collected from the duct. Some of the lavage or washing fluid can remain in the duct. Massaging and/or squeezing a duct that has been infused with lavage fluid results in a better yield of ductal fluid and cells from origins of all areas of the duct, including and especially distal areas of the ductal architecture, as compared to yields of fluid and cells from flushing alone (e.g. simple lavage without massaging and/or squeezing).

Collection can comprise placing an outflow lumen in the duct for directing fluid in the duct outwards. Tubes can be positioned or placed at the outside end of the outflow lumen for collecting fractions. The fractions can be collected serially, e.g. in aliquots of the same size or about the same size. A process of continuous infusion of lavage fluid, squeezing and collecting the fractions can proceed in order to collect a representative sample of fluid and cells from the ducts so that accurate analysis of the condition of the duct can be made by analyzing this fluid and cells. The lavage fluid can be continuously infused over a period of time, during which the duct is filled and optionally remains full during massaging and/or squeezing and collection due to the continuous infusion of new lavage fluid into the duct.

The periodicity of application of external pressure can comprise e.g. massaging and/or squeezing the breast (e.g. manually) after an infusion of lavage fluid that fills the duct and collecting the fluid; massaging and/or squeezing continuously during continuous infusion of the lavage fluid and continuous collection; or intermittent massaging and/or squeezing as the breast is filled and emptied and refilled with corresponding collection of the fluid fractions that result. individual practitioners will determine a combination of efforts that will work best for them and their patients and which will result in the optimal yield of fluid and cells with minimal trauma to the breast tissue of the patient. In all cases it is important not to rupture the ductal architecture with massaging and/or squeezing that is too vigorous and in no case is it intended that the massaging and/or squeezing should be performed to a degree that threatens damage to the breast tissue to the extent that compromises the integrity of ductal structures inside the breast.

Collecting the fluid from the duct can be further aided by applying suction to the end of an outflow lumen that extends from a duct accessed by a dual lumen catheter. The suction can be applied using a device capable of creating suction in a lumen, e.g. a syringe or other suction device positioned at the end of the outflow lumen that extends outside the duct. The application of suction at the outflow lumen may be brief, e.g. to establish the ductal fluid flowing from inside to outside the duct, or the suction may be applied for a more extended period of time during the procedure, e.g. during a corresponding continuous infusion of lavage fluid into the inflow lumen.

The lavage or washing fluid can further comprise air mixed in with the fluid for delivery into the duct. The presence of air or other gas may serve to increase the retrieval of cells and fluid as compared to lavage with fluid not having air or gas bubbles mixed in with the fluid. The air can be introduced into the fluid by standard means, including by introduction of air or gas from a pressurized container.

The invention comprises a kit for obtaining material from a milk duct of a breast. The kit can comprise an access tool having at least one lumen. Thus, the access tool could be, e.g. a single lumen catheter, a dual lumen catheter, a multi-lumen catheter, a cannula, hollow probe, or other access tool having at least one lumen. The kit can further comprise instructions setting forth a method for use of the access tool according to the methods and embodiments that include applying external pressure to the breast as described above. The instructions can include detailed guidance and description for the application of manual or mechanical massage. A kit for applying external pressure mechanically will comprise a tool for applying the mechanical pressure. Instructions for a kit that directs application of external pressure to the breast manually will comprise instructions detailing ways to massage and/or squeeze the breast most effectively during the lavage procedure, including, e.g. such details as described above. The instructions can include a description complete with illustrations and suggested approaches for massaging and/or squeezing of the breast that can be applied during the lavage procedure. The kit can also include a device for providing suction to an outflow lumen, e.g. a syringe, and additional directions for how to apply the suction. The suction applied can be approximately reciprocal with the flow of fluid into the duct from the inflow lumen. The strength and rate of the outflow pressure possible will depend on such variables as the size of the duct, the amount of fluid in the duct, and the strength and rate of the inflow pressure. The collected fluid may be treated or analyzed in conventional ways to identify the presence, amount(s), identities, and/or other characteristics of any marker materials that may be present in the collected fluids. For example, cellular materials may be transferred to a suitable medium, such as RPMI or other growth or maintenance medium. The cells may then be examined morphologically under a microscope and/or histologically using suitable histochemical and immunochemical staining reagents. Chemical and molecular markers may be identified and/or examined chemically, immunologically, enzymatically, or by other conventional techniques. Such analysis techniques are well described in the art.

Kits according to the present invention will comprise at least a catheter 50 (which may be any dual- or multiple-lumen catheter capable of accessing an individual ductal network) and instructions for use (IFU) 80 which are combined together in a conventional manner, typically within a container 82, which may be in the form of a pouch, tray, box, tube, or the like. Kits will usually also include at least a guidewire, and other kit components may also be provided. For example, a syringe 84 may be provided, usually pre-filled with saline or other suitable washing medium for washing the ductal network. Additionally, a collection tray 86 for receiving and maintaining the cellular material and the washing fluids collected from the catheter may also be provided. Optionally, the tray may include a suitable collection medium, such as RPMI medium. Still further, the kits may include materials for assaying non-cellular markers as well as components for identification of the ductal orifice, such as described in co-pending application Ser. No. 08/931, 786, the full disclosure of which was previously incorporated herein by reference.

The following examples are offered by way of illustration, not by way of limitation.

EXPERIMENTAL

Figure 7A:
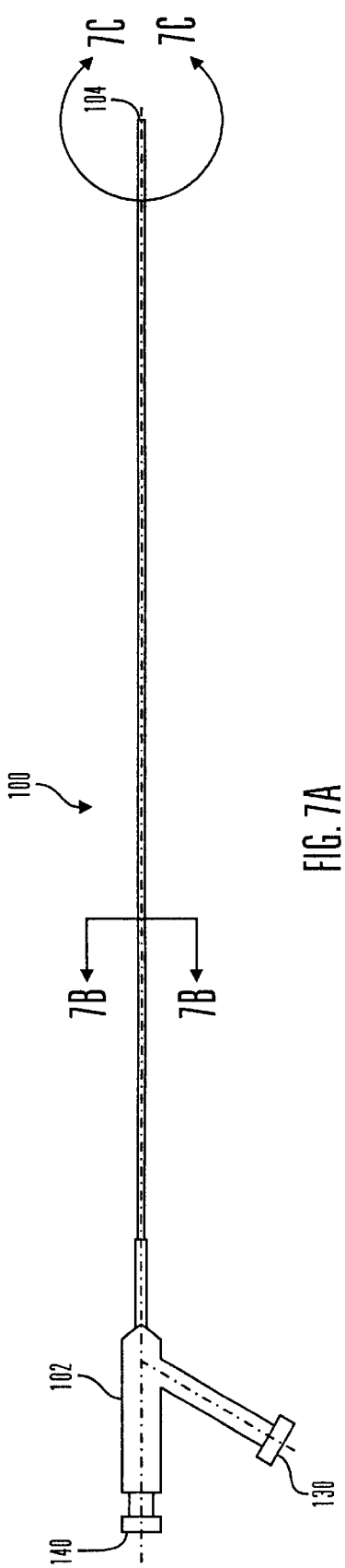
FIGS. 7A–7C illustrate the catheter utilized in the working examples hereinafter.
Figure 7C:
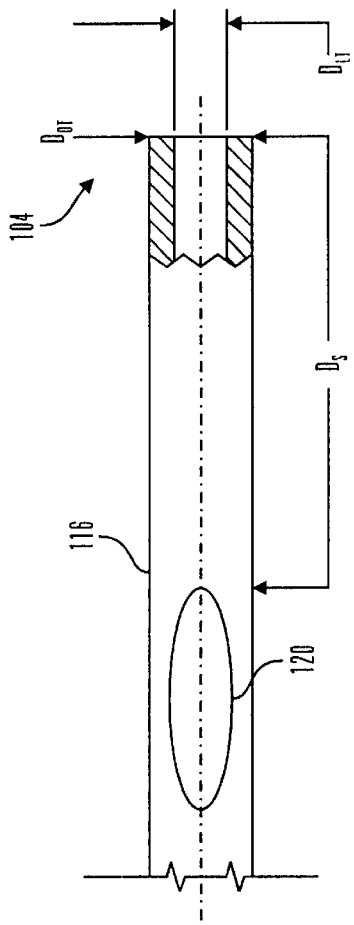
Figure 7B:
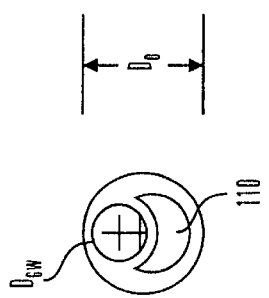

A double lumen catheter which would allow a continuous flow of saline throughout the ductal system was prepared, as illustrated in FIG. 7. The catheter was a 3 French double lumen catheter with the proximal lumen smaller in diameter and the distal larger to allow aspiration. In particular, the catheter 100 had a length from the hub 102 to the distal tip 104 of 31 cm, an outer diameter of $D_O$ of 0.041 in, a guidewire lumen $D_{GW}$ of 0.019 in, and a crescent-shaped lumen 110. The outer tip diameter $D_{TO}$ was 0.033 in and the lumenal tip diameter $D_{LT}$ was 0.017 in, reflecting a tapered distal end 116. A side port 120 having an oval geometry of 0.07 in×0.016 in formed the distal end of the lumen 110 and was spaced-proximally of the distal tip by a distance $D_S$ of 0.16 in. Fluid was introduced through port 130 and lumen 110 out through side port 120 into the ductal lumen. Fluid was collected through the distal tip and back through the guidewire lumen (after withdrawing the guidewire), and then through port 140. Initially the catheter was tested in breasts that had been removed surgically. Ten breasts were studied and cells were retrieved from seven. The catheter was also used with twelve anesthetized women prior to breast surgery. Cells were retrieved from ten of the twelve (83%). See Table 1.

Materials and Methods

After general anesthesia had been administered, the patient's breast was prepped and draped. Mild suction was applied to the nipple to try to elicit discharge. A dissecting microscope or loupe was used to magnify the nipple and identify orifices. A map was made of the identified orifices. Starting with the most promising orifice (i.e. most amount of discharge, and/or the largest), attempts were made to cannulate one or more orifices using either a standard set of metal dilators (galactography set by Mahan), or a very small guide wire of the type used in angiography. Once the duct had been cannulated and dilated to approximately 0.7–1.0 mm, the double lumen catheter was threaded into the duct. Saline was instilled, setting up a continuous flow until 10 cc was collected. The procedure took about 15 minutes. If 10 cc of fluid was not collected within the 15 minute limit, the procedure stopped prematurely. The washings were then sent to cytology for analysis.

Results

The results are show in Table 1.

TABLE 1

| patient # | breast | mass location | duct location | #duct | pathology | cytology |
|---|---|---|---|---|---|---|
| Detached breasts | | | | | | |
| 1 | R | RLQ | central | 1 | Ductal carcinoma comedo | acellular |
| 2 | R | No cancer | 6:00 | 3 | | ductal cells |
|   | L | L breast | 9:00, 7:00 | 3 | Micropapillary DCIS | ductal cells |
| 3 | L | LLQ | 12:00 | 3 | infiltrating ductal carcinoma | ductal cells |
| 4 | R | RUOQ | 8:00 | 4 | DCIS pagetoid | ductal cells |
| 5 | L | LUOQ | 11:00 | 5 | Intraductal carcinoma in situ | ductal cells |
| 6 | R | no cancer | 9:00 | 2 | | acellular |
|   | L | 3:00, 9:00 | 6:00 | 4 | Invasive ductal carcinoma, DCIS | acellular |
| 7 | L | LUOQ | 6:00 | 4 | Infiltrating ductal carcinoma, DCIS | (1) acellular, (2) ductal cells |
| 8 | L | LOQ, 3:00 | central | 2 | Infiltrating lobular carcinoma, infiltrating ductal | ductal cells |
| Attached breasts | | | | | | |
| 1 | R | RUOQ | 12:00 | 2 | adeno ca | carcinoma cells |
| 2 | L | retroaerolar | central | 1 | poorly diff. ductal carcinoma | deteriorated cells |
| 3 | R | RUOQ | 3:00 | 3 | tubular carcinoma, micropapillary | deteriorated cells |
| 4 | L | infraaerolar | 9:00 | 2 | invasive ductal carcinoma | deteriorated cells |
| 5 | R | N/A (abscess) | central | 1 | lactiferous duct | Acellular |
| 6 | L | LUOQ | 3–4:00 | 1 | fiberadenoma | Benign mammary epithelial cells |
| 7 | R | | 3:00 | | fibroadenoma | Abund epithelial cells, benign |

TABLE 1-continued

| patient # | breast | mass location | duct location | #duct | pathology | cytology |
|---|---|---|---|---|---|---|
| 8 | R | 12:00 | 12:00 | 2 | Invasive ductal carcinoma | mammary epithelial cells Acellular, rare, ductal cells |
| 9 | R | 11:00 | 11:00 | 3 | Invasive lobular | acellular |
| 10 | L | UOQ | central | 1 | Invasive lobular | Mod macrophage, no ductal cells |
| 11 | L | LUOQ | central | 1 | Adeno carcinoma | Foam cells, ductal cells |
| 12 | R | RUOQ | 3:00 | 2 | Atyp med carcinoma | Foam cells, rare ductal cells |

R: right
L: left
RLQ: right lower quadrant
LLQ: left lower quadrant
LUOQ: left upper outer quadrant
LOQ: left outer quadrant
RUOQ: right upper outer quadrant
UOQ: upper outer quadrant
DCIS: ductal carcinoma in situ

EXAMPLE 2

Retrieval of Chinese Ink from Pig Nipples

The purpose of this experiment was to determine the efficiency of the method of the invention in performing ductal lavage with a double lumen catheter in pig breasts using massaging and/or squeezing in order to retrieve fluid from the breast milk ducts including regions distal to the lactiferous sinus in those ducts. Three experiments were conducted, each to test slightly different parameters of the lavage and fluid retrieval process.

A. An aliquot of 3 ml of Chinese ink (black color) was infused into a pig duct A on nipple A by single lumen catheter. The single lumen catheter was removed and the breast squeezed resulting in the retrieval of 0.7 ml of ink (i.e. very black fluid). A double lumen catheter was inserted and the duct was flushed with about 10 ml of phosphate buffered saline (PBS). From the outflow lumen of the catheter, fluid was collected serially in 3 tubes, at a volume of about 1 ml each. The first tube (T1) yielded black fluid, and the second and third tubes (T2, T3) yielded clear fluid. The duct was flushed with another 10 ml of PBS and at the same time the breast was massaged and squeezed. The outflow was collected in 4 tubes, of about 1 ml aliquot in each tube. T4–T7 all yielded black fluid. The duct was flushed with a third aliquot of 10 ml of PBS. Three aliquots of 1 ml each were collected without massaging and squeezing. T8 fluid was black, T9 fluid was light black, and T10 fluid was clear. The breast was massaged and squeezed and another 3 tubes of about 1 ml each were collected (T11, T12, and T13) all black in color. In summary, the total injected ink was 3 ml, and the total infused PBS was 30 ml for a total of 33 ml of fluid. Approximately 15.7 ml of fluid and ink was retrieved (in 13 tubes) leaving about 17.3 ml of fluid in the duct. After the lavage experiment was completed, the breast was excised to examine the ductal network. The duct was intact, and thus the lavage procedure had been performed on an intact ductal system.

B. An aliquot of 0.5 ml of Chinese ink was infused into pig duct B on nipple B by single lumen catheter. An aliquot of 5 ml of PBS was infused into the same duct by the same single lumen catheter to push the Chinese ink into the distal regions of the duct. The single lumen catheter used for injection of fluid in this manner was to quantitate precisely the amount of fluid infused into the duct. The single lumen catheter was removed and the breast and nipple massaged and squeezed. An aliquot of 0.3 ml of black ink/fluid was collected (tube T1). A double lumen catheter was inserted into the duct and the duct was flushed with 10 ml of PBS. The first two collections of 1 ml each were done without massaging or squeezing. T2 yielded black fluid and T3 yielded clear fluid. Then massaging and squeezing actions were used to collect 1 ml aliquots in 4 more tubes: T4, T5, T6, and T7 yielded black fluid. 10 ml more of PBS was infused into the duct and massaging and squeezing was applied to yield 4 tubes of 1 ml each of black fluid (T8–T11). T12 was fluid collected with flushing only, and the fluid was clear. 10 ml more of PBS was infused into the duct, followed by and concurrent with massaging and squeezing to collect 5 tubes of 1 ml each, T13–T17; all the fluid collected in these tubes was black. To summarize, the total infused volume of ink and PBS was about 35.5 ml; about 17.3 ml of fluid was collected (in 17 tubes), and the estimated fluid remaining in the breast was about 18.2 ml. The experiment showed that ductal lavage with massaging and squeezing could retrieve infused Chinese ink from distal regions of the breast milk duct. The breast was excised and analyzed to show that no penetration or leaking occurred in the accessed duct.

C. Duct C on nipple C was infused with 0.1 ml of Chinese ink by single lumen catheter. The same catheter was used to inject 8 ml of PBS immediately following the infusion of ink. The catheter was removed and the breast massaged and squeezed to yield 50 ul of black fluid (0.05 ml). A double lumen catheter was inserted and the duct flushed with PBS by the combination of flushing, massaging and squeezing (flushing with 10 ml of PBS each time, for a total of 30 ml), and the fluid collected in 22 tubes (of about 1 ml each). To summarize, the total fluid infused into the duct (including the ink) was 38.1 ml; about 22.05 ml was collected. The fluid left in the breast was estimated to be about 16.05 ml. The breast was excised and analyzed for ductal rupture or leakage and neither were found. To quantitate the recovery of infused ink, the 22.05 ml was brought to a volume of 40 ml with PBS, and a control tube was made with 0.1 ml of ink plus 39.9 ml of PBS, for a total volume for the control of 40 ml. Serial dilutions of each sample were made, e.g. $\frac{1}{2}$, $\frac{1}{4}$, $\frac{1}{8}$, $\frac{1}{16}$, $\frac{1}{32}$, $\frac{1}{64}$. The dilution of $\frac{1}{8}$ was used in both samples to do a wavelength scan on a spectrophotometer to determine which wavelength is optimal for reading for Chinese ink. Light absorption for each sample was recorded at 224 and 227 nm. The recovery rate from the wash fluid was calculated as follows:

rate=test sample optical density (OD) divided by control OD in the same dilution The results of the entire set of Chinese ink experiments indicate that duct lavage using a combination of flushing with PBS and concomitant and/or subsequent massaging and/or squeezing of the breast can wash not only the lactiferous sinus, but also more distal regions of the ductal architecture as well. The experiments also demonstrated that the lavage procedure with a dual lumen catheter resulted in a maintenance of the structural integrity of the ducts that were lavaged.

See Table 2 for the yield results from pig Ducts A & B.

Table 3 reports the absorption values for the Chinese ink-containing fluid yielded from Duct C. From these values using the rate above, an 87.5% average yield was determined. E.g. at absorption of wavelength of 227 nm, at 1/32 dilution the sample yielded absorption of 0.2803; this value divided by the absorption of the control at 1/32 dilution (0.3272 value) yields 0.86. For 1/16 dilution, sample value 0.5824 divided by control value 0.6801 (both at 227 nm) yielded 0.86; and for dilution 1/8, sample value 1.0897 divided by control value 1.2332 yielded 0.88; for dilution 1/4 sample value 2.4340 divided by control value 2.7111 yielded 0.90; for an average of the 4 values of 87.5% recovery in the sample tubes.

TABLE 2

Fluid & Ink Recovery Ducts A & B

| | Duct | tube/yield | action taken | color of collected fluid |
|---|---|---|---|---|
| 1 | A | T0/0.7 ml | 3 ml of ink was injected into the nipple and the nipple squeezed | black |
| 2 | A | T1 | 10 ml of PBS was infused into the nipple and 3 tubes used to collect fluid - no massaging or squeezing | black |
| 3 | A | T2 | 10 ml of PBS was infused into the nipple and 3 tubes used to collect fluid - no massaging or squeezing | clear |
| 4 | A | T3 | 10 ml of PBS was infused into the nipple and 3 tubes used to collect fluid - no massaging or squeezing | clear |
| 5 | A | T4 | 10 ml of PBS was infused and this time massaging and squeezing was used during infusion and fluid collection in 4 tubes | black |
| 6 | A | T5 | 10 ml of PBS was infused and this time massaging and squeezing was used during infusion and fluid collection in 4 tubes | black |
| 7 | A | T6/ | 10 ml of PBS was infused and this time massaging and squeezing was used during infusion and fluid collection in 4 tubes | black |
| 8 | A | T7 | 10 ml of PBS was infused and this time massaging and squeezing was used during infusion and fluid collection in 4 tubes | black |
| | A | T8/ | 10 ml of PBS was infused and fluid collected serially in 3 tubes of 1 ml each; no squeezing of massaging was used | black |
| 9 | A | T9 | 10 ml of PBS was infused and fluid collected serially in 3 tubes of 1 ml each; no squeezing of massaging was used | light black |
| 10 | A | T10 | 10 ml of PBS was infused and fluid collected serially in 3 tubes of 1 ml each; no squeezing of massaging was used | clear |
| 11 | A | T11 | the breast was massaged and squeezed | black |
| 12 | A | T12 | the breast was massaged and squeezed | black |
| 13 | A | T13 | the breast was massaged and squeezed | black |
| 14 | B | T1/0.3 | 0.5 ml of black ink was infused into the duct; by squeezing and massaging some fluid was collected | black |
| 15 | B | T2 | 10 ml of PBS was infused into the duct using the new dual lumen catheter; the first two collections of about 1 ml each were made without massaging or squeezing | black |
| 16 | B | T3 | 10 ml of PBS was infused into the duct using the new dual lumen catheter; the first two collections of about 1 ml each were made without massaging or squeezing | clear |
| 17 | B | T4 | then massaging and squeezing was used to collect 4 aliquots of 1 ml each | black |
| 18 | B | T5 | then massaging and squeezing was used to collect 4 aliquots of 1 ml each | black |
| 19 | B | T6 | then massaging and squeezing was used to collect 4 aliquots of 1 ml each | black |
| 19 | B | T7 | then massaging and squeezing was used to collect 4 aliquots of 1 ml each | black |
| 20 | B | T8 | 10 ml of PBS was infused and 4 tubes were used to serially collect 1 ml aliquots; massaging and squeezing was used throughout the collection procedure | black |
| 21 | B | T9 | 10 ml of PBS was infused and 4 tubes were used to serially collect 1 ml aliquots; massaging and squeezing was used throughout the collection procedure | black |
| 22 | B | T10 | 10 ml of PBS was infused and 4 tubes were used to serially collect 1 ml aliquots; massaging and squeezing was used throughout the collection procedure | black |
| 23 | B | T11 | 10 ml of PBS was infused and 4 tubes were used to serially collect 1 ml aliquots; massaging and squeezing was used throughout the collection procedure | black |
| 24 | B | T12 | fluid was collected for this tube using flushing only, no massaging and squeezing | clear |

TABLE 2-continued

Fluid & Ink Recovery Ducts A & B

| | Duct | tube/yield | action taken | color of collected fluid |
|---|---|---|---|---|
| 25 | B | T13 | 10 ml of PBS was infused and 5 more tubes were used to serially collect 1 ml each of fluid | black |
| 26 | B | T14 | 10 ml of PBS was infused and 5 more tubes were used to serially collect 1 ml each of fluid | black |
| 27 | B | T15 | 10 ml of PBS was infused and 5 more tubes were used to serially collect 1 ml each of fluid | black |
| 28 | B | T16 | 10 ml of PBS was infused and 5 more tubes were used to serially collect 1 ml each of fluid | black |
| 29 | B | T17 | 10 ml of PBS was infused and 5 more tubes were used to serially collect 1 ml each of fluid | black |

TABLE 3

Absorbance of Sample vs. Control

| sample ID | 224 nm wavelength | 227 nm wavelength |
|---|---|---|
| control 1/64 | 0.1244 | 0.1365 |
| control 1/32 | 0.3088 | 0.3272 |
| control 1/16 | 0.6527 | 0.6807 |
| control 1/8 | 1.1899 | 1.2332 |
| control 1/4 | 2.6388 | 2.7111 |
| control 1/2 | 3.5350 | 3.5562 |
| control 1 | 3.4839 | 3.5562 |
| sample 1/64 | 0.1445 | 0.1543 |
| sample 1/32 | 0.2712 | 0.2803 |
| sample 1/16 | 0.5720 | 0.5824 |
| sample 1/8 | 1.0854 | 1.0897 |
| sample 1/4 | 2.4469 | 2.4340 |
| sample 1/2 | 3.3967 | 3.4593 |
| sample 1 | 3.6600 | 3.5562 |

EXAMPLE 3

Collection of Cells in Milk Duct Lavage Fluid from a Pig Pelt Using Fluid Infusion, Squeezing, Massage & Suction The purpose of the experiment was to determine the efficiency of a lavage procedure with and without squeezing and massage by checking the cell density of the retrieved fluid and cells in serially collected fractions of pig milk duct fluid.

A pig pelt having 4 breasts was obtained for the experiment. Four pig ducts in 4 nipples were lavaged with a dual lumen catheter (Fuji I) for breast duct fluid aspiration with PBS.

The Fuji I dual lumen catheter is specially constructed for Windy Hill Technology (item IEE 4N WH081598-1) by Infinity Extusion & Engineering, located at Santa Clara, Calif.; the catheter has the following specifications: 0.024" outer diameter of infusion lumen; 0.019" inner diameter of infusion lumen; 0.017" inner diameter of collection lumen; length of catheter is 40 cm; made of polymer material; depth markers located on the catheter at 0.6, 0.8, 1.0, and 1.2 cm.

For each duct, the dual lumen catheter was inserted into the pig milk duct. The flushing occurred with PBS from the inflow lumen of the catheter, and the lavage fluid was collected from the outflow lumens. The first 2 tubes were collected. The outflow lumen was closed and then enough fluid was infused until resistance was felt (about 5 ml of PBS). The breast and nipple of the pelt was massaged and squeezed and suction was applied to the outflow lumen to collect lavage fluid. New PBS fluid was infused periodically to a point of resistance and the breast and nipple massaged and squeezed, and the fluid retrieved by suction at the outflow: e.g. massage; squeeze; suction⟳infusion⟳massage; squeeze; suction⟳infusion⟳repeated several times. A total of about 30 to 35 ml lavage fluid was infused per duct. The lavage fluid was serially and fractionally collected in volumes of about 1 ml per tube. Total collection amount for each duct was 12 tubes of about 1 ml each; the first 2 ml collected without squeezing, massage or suction, and the remaining 10 tubes collected by cyclic infusion, massaging and squeezing etc. as just described. Tubes 1 and 2 (T1 & T2) collected fluid from flushing alone. Tubes 3–12 (T3–T12) collected fluid resulting from a combination of flushing along with massage and squeezing of the breast and nipples and suction applied to the outflow catheter with a syringe.

Cells collected from each fraction were spun out on a glass slide for analysis. An aliquot of 50 ul of collected fluid from each tube was used to prepare a Cytospin™ slide using cytospin 3 cytocentrifuge (Shandon Lipshaw, located at Pittsburgh, Pa.). The cells were air dried and stained by Diff-Quik™ method (available from Dade Behring, Inc., Newark, Del. distributors; stain made in Switzerland by Dade Behring) The cell density of each slide was estimated by percent similarity of cell culture confluence.

The results of the collections and analysis of the prepared cells is reported in Table 4. The conclusions that can be drawn from this experiment are that lavage with squeezing (including massaging) and suction increased cell numbers in the lavage fluid collected as compared to the cell numbers collectable with simple lavage without squeezing or suction. The lavage procedure with massaging and squeezing and suction retrieves cells not only from the lactiferous ducts and sinus, but also from regions of the ductal architecture more distal than the sinus, as indicated by the cell retrieval before and after massaging and squeezing in these fractional collection experiments.

EXAMPLE 4

Lavage of Live Rabbit Milk Ducts With Squeezing and Massage to Yield Cells Having an Origin in the Duct Distal to the Lactiferous Sinus New Zealand rabbits from Kralek Farm (located in Turlock, Calif.) were used for the experiment. Rabbits WHT #8 and WHT #9 were used. The rabbit milk ducts were lavaged with PBS using a modified Fuji I catheter. The modified Fuji I dual lumen catheter is specially made as described in Example 3, with additional size modifications for use in rabbits. Lavage fluid was serially and fractionally collected in amounts of about 200 ul per tube. The first two fractions from each duct were collected from retrieval of flushing fluid without application of external pressure to the breast. The subsequent four fractions were collected after fluid infusion followed by and concurrent with squeezing and massaging of the breast and nipple.

Each 200 ul fraction was used to prepare a Cytospin™ slide (Shandon Lipshaw, located at Pittsburgh, Pa.). The cells were air-dried and stained by Diff-Quik™ method (available from Dade Behring, Inc., Newark, Del. distributors; stain made in Switzerland by Dade Behring). Six ducts from rabbit WHT #8 were lavaged, and thus 6 fractions were collected from each duct for a total of 36 fractions of 200 ul each, and a corresponding 36 slides. Five ducts were lavaged from WHT #9, 6 fractions were collected from each duct for a total of 30 fractions of 200 ul each, and a corresponding 30 slides. Cell type and cell number were evaluated from these slides. The cytology is described as follows: "Clusters" of cells contain greater than 11 cells in an epithelial clump; "Groups" of cells contain from about 4 to 10 cells in an epithelial clump; "Mixed cells" include macrophages, foam cells, leukocytes, and individual epithelial cells (including e.g. single, double or triplet cells). The "Cell Number" of the mixed or individual cells was determined by looking at a slide under a microscope at 40X magnification and taking an average count of 4 fields on that slide. For the mixed cells of lesser amounts than could be counted in a 40X objective field: "Few" represents less than 50 total cells in each slide; "Scattered" represents more than 50 cells in a slide, but not enough to be counted per 40X objective field.

The results of the experiment are shown in Table 5, and indicate a bolus of cells retrieved with an initial flushing fraction (Tubes 1) followed by a low retrieval on the second flushing fraction collection (Tubes 2). Upon addition of infusion of more fluid and massaging and squeezing , a new bolus of cells were retrieved (Tubes 3). The experiment demonstrates the value and requirement of massaging and squeezing in a lavage procedure in order to retrieve cells in the ductal system distal of the lactiferous duct and sinus.

TABLE 5

| Rabbit & Tube # | EPITHELIAL CLUMP | | | MIXED CELLS | | |
|---|---|---|---|---|---|---|
| | Cluster #/ducts | Group #/ducts | # per 40x #/ducts | scattered (ducts) | few (ducts) | no cells (ducts) |
| WHT#8-1 | 101/5 | 122/5 | 115/2 | 2 | 2 | — |
| WHT#8-2 | 31/3 | 37/3 | 39/2 | 1 | 2 | 1 |
| WHT#8-3 | 116/5 | 152/5 | 118/2 | 4 | — | — |
| WHT#8-4 | 54/4 | 46/4 | 39/2 | 2 | 1 | 1 |
| WHT#8-5 | 25/2 | 35/3 | 58/2 | 1 | 2 | 1 |
| WHT#8-6 | 13/3 | 21/2 | 16/1 | 1 | 3 | 1 |
| WHT#9-1 | 68/4 | 87/3 | 75/3 | — | 1 | — |
| WHT#9-2 | 30/3 | 24/3 | 43/3 | — | 1 | 1 |
| WHT#9-3 | 70/4 | 68/4 | 132/5 | — | — | — |
| WHT#9-4 | 4/1 | 11/2 | 117/2 | 2 | 1 | — |
| WHT#9-5 | 8/3 | 17/3 | 52/4 | — | 1 | 1 |
| WHT#9-6 | 9/3 | 13/3 | 39/3 | 1 | — | 1 |

EXAMPLE 5

Dye Recovery and Cell Yield by Ductal Lavage of Human Patient Using Massaging and Squeezing A 47-year old female patient (ID #9025) volunteered for the lavage and massaging and squeezing procedure of a single milk duct. Local anesthesia was administered to the right nipple in a sealed block by subcutaneous injection of lidocaine (without epinephrine) from the periphery of the areola to the nipple. The physician administered a total volume of 10 cc of lidocaine (concentration 10 mg/ml) using multiple injections.

A ductal orifice on the right breast was accessed by a series of galactography dilators (available from Medical Device Technologies, Inc., Gainsville, Fla.) increasing in size in order to dilate the ductal orifice and provide an opening large enough to permit access by a dual lumen catheter.

A Fuji I dual lumen catheter, made as described in Example 3, was inserted into the duct after removal of the largest galactography dilator. The duct was infused with 1 cc of 1% lymphazurin dye (manufactured for U.S. Surgical Corp., Norwalk, Conn. 06858 by Ben Venue Labs, Inc. Bedford, Ohio 44146). Following the dye infusion, 5 cc of saline were infused using the same catheter. The duct was then infused with more saline. During the flushing (infusion), the outflow fluid was collected in 4 tubes, of about 1 cc each (tubes T1–T4). No massaging or squeezing was applied to the breast or nipple. The color of the liquid collected in the tubes changed from blue (T1) to very light blue (T4). For collection of a final sample, the breast was massaged and squeezed and a fifth tube of about 1 cc was collected (T5). T5 was blue in color. The fluid color was measured by spectrophotometer at the peak optical density (OD) for lymphazurin (634 nm wavelength). The results are shown in Table 6.

The fluid samples were spun in a centrifuge (IEC Centra CL3R; available from Shandon Lipshaw, located at Pittsburgh, Pa.) at 2500 rpm for 10 minutes. The supernatant was discarded. The cells were suspended in 100 ul of PBS. Each tube/sample was spun onto a glass slide using the Cytospin® centrifuge and the cells were air dried. The cells on the slide were stained with Diff-Quik® stain (available from Dade Behring, Inc., Newark, Del. distributors; stain made in Switzerland by Dade Behring) The results of the cell recovery are shown in Table 6. The cells were counted and classified as described in Example 4, and Table 5. The last tube, T5 yielded significantly more cells as a result of the massaging and squeezing than the previous tube T4 which collected the last in the series of collections made without the benefit of massaging and squeezing the breast.

TABLE 6

| Tubes/action | -OD @ 634 nm | Epithelial Cluster | Epithelial Group | Mixed Cells per 40x lens field |
|---|---|---|---|---|
| T1/flushing only | not done | 93 | 105 | 62 |
| T2/flushing only | 4.5 | 10 | 24 | 17 |
| T3/flushing only | 4.5 | 29 | 63 | 34 |
| T4/flushing only | 1.2 | 2 | 7 | scattered |
| T5/lavage + massaging and squeezing | 4.5 | 11 | 17 | 42 |

EXAMPLE 6

Cell Yield by Ductal Lavage of Human Patient Using Massaging and Squeezing

Human female patient (69 years old) ID #9014 was lavaged in a single duct to demonstrate that cell yield is increased and optimized upon lavage techniques combined with squeezing and massaging of the breast. Serial and fractional fluid samples were collected during the lavage procedure, and the samples were analyzed to quantify cell yield. Local anesthesia was administered to the right nipple in a sealed block by subcutaneous injection of lidocaine (without epinephrine) from the periphery of the areola to the nipple. The physician administered a total volume of 12 cc of lidocaine (concentration 10 mg/ml) using multiple injections.

A ductal orifice on the right breast was accessed by a series of galactography dilators (available from Medical Device Technologies, Inc., Gainsville, Fla.) increasing in size in order to dilate the ductal orifice and provide an opening large enough to permit access by a dual catheter lumen.

A Fuji I catheter (see Example 3 above) having a dual lumen was inserted into the duct. The duct was flushed with saline, and this first fluid was collected in a tube at the outflow lumen (T1=1 cc). Lavage fluid was then continuously introduced and the breast was massaged and squeezed. Fluid was serially and fractionally collected in three tubes (T2, T3, and T4), collecting a volume of about 1 cc in each tube. The tubes were spun in the centrifuge as described in Example 5, resuspended in 100 ul PBS, and spun onto slides as described in Example 5. The results of the quantification of cells on each slide are shown in Table 7 and can be summarized as follows: T1 yielded only a few individual cells; T2 and T3 (collected after and during massaging and squeezing) yielded more than 100 mixed cells per 40X objective lens field (under a microscope); T4 (also collected during and after magnification) yielded 34 cells per 40X objective lens field.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for obtaining fluid and cellular material from a breast duct including fluid and cellular material from distal areas of the ductal architecture of a breast milk duct comprising:
    (a) locating at least one milk duct on a nipple of a breast, wherein the milk duct exhibits no observable spontaneous discharge;
    (b) introducing washing fluid into the milk duct, and providing continuous or intermittent infusion of the wash fluid for a period of time;
    (c) applying external positive pressure to the breast and repeating application of external pressure periodically, continuously, or cyclically during infusion of the wash fluid; and
    (d) collecting the washing fluid intraductally from the duct during the infusion and application of external pressure, wherein the washing fluid collected comprises fluid and cells from the duct.

2. The method of claim 1, wherein the pressure is applied manually or mechanically.

3. A method as in claim 1, wherein introducing and collecting comprise access of a breast duct by an access tool having at least one lumen.

4. The method of claim 3, wherein collecting comprises applying suction to an outflow lumen of a dual lumen catheter to draw fluid out from the duct.

5. A method of obtaining material from a milk duct in a breast of a patient comprising:
    (a) locating at least one ductal orifice on a nipple of the breast, wherein the at least one ductal orifice exhibits no observable spontaneous discharge;
    (b) introducing an access tool having at least one lumen through one of the ductal orifices and into the ductal passage;
    (c) introducing a washing fluid through a lumen into the ductal passage;
    (d) applying external positive pressure to the breast and repeating application of external pressure periodically, continuously, or cyclically during infusion of the wash fluid; and
    (e) collecting the washing fluid intraductally from the ductal passage through a lumen of the access tool during or after fluid introduction and application of external pressure to the breast.

6. The method according to any claims 1 or 5, wherein the washing fluid comprises a mixture of air fluid.

7. A method as in claim 1, wherein about 5 ml to about 20 ml of washing fluid is introduced into the milk duct.

8. A method as in claim 5, wherein about 5 ml to about 20 ml of washing fluid is introduced into the milk duct.

9. A method as in claim 1, wherein the washing fluid is continuously or intermittently infused in volumes of about 0.5 ml to about 1.0 ml at a time.

10. A method as in claim 5, wherein the washing fluid is continuously or intermittently infused in volumes of about 0.5 ml to about 1.0 ml at a time.

11. A method as in claim 1, wherein introducing washing fluid comprises introducing a sufficient amount of washing fluid to substantially fill the duct.

12. A method as in claim 5, wherein introducing washing fluid comprises introducing a sufficient amount of washing fluid to substantially fill the duct.

13. A method as in claim 1, wherein the pressure is applied beginning at the base of the breast and moving towards the areola and nipple regions of the breast.

14. A method as in claim 5, wherein the pressure is applied beginning at the base of the breast and moving towards the areola and nipple regions of the breast.

15. A method as in claim 5, wherein the pressure is applied manually.

* * * * *